United States Patent
Hawthorne et al.

(10) Patent No.: US 6,355,840 B1
(45) Date of Patent: Mar. 12, 2002

(54) SYNTHESIS OF PERMETHYLDODECABORATE AND PARAMAGNETIC DODECABORATE SALT

(75) Inventors: M. Frederick Hawthorne, Encino; Toralf Peymann, Los Angeles, both of CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/576,842

(22) Filed: May 23, 2000

(51) Int. Cl.[7] ................................................. C07F 5/02
(52) U.S. Cl. ............................................. 568/3; 568/4
(58) Field of Search ........................... 568/3, 4; 423/276

(56) References Cited

PUBLICATIONS

J Am. Chem. Soc. by Peymann et al 121 pp. 5601–5602, year 1999.*

Toralf Peymann, Carolyn B. Knobler, and M. Frederick Hawthorne, An Icosahedral Array of Methyl Groups Supported by an Aromatic Borane Scaffold: The [closo–B$_{12}$(CH$_3$ ) ]$^{2-}$Ion, J. Am. Chem. Soc. May 29, 1999, 121, pp. 5601–5602.

Toralf Peymann, Carolyn B. Knobler, and M. Frederick Hawthorne, An Unpaired Electron Incarcerated within an Icosahedral Borane Cage: Synthesis and Crystal Structure of the Blue, Air–stable {[colso–B$_{12}$ (CH$_3$) ]} radical, Chem. Commun., 1999, pp. 2039–2040.

M. Frederick Hawthorne, Broadening The Conflux of Boron and Carbon Chemistries,Dept. of Chemistry, University of California, Los Angeles, (presented in Durham, UK, Jul. 12, 1999), 8 pages.

Wei Jiang, Carolyn B. Knobler, and M. Frederick Hawthorne, Decakis (dchloromethyl)–1, 12–dicarba–closo–dodecaborane (12): CAmouflage of an Icosahedral Carborane By Using Bulky Functional Substituents, Angew. Chem. Int. Ed. Eng 1, 1996, 35, No. 21, pp. 2536–2537.

M.Frederick Hawthorbne, Carborane Chemistry At Work and At Play, Dept. of Chemistry and Biochemistry, The University of California, Los Angeles, (Presented at the Royal Society, UK 1996) pp. 1–17.

* cited by examiner

*Primary Examiner*—Jean F. Vollano
(74) *Attorney, Agent, or Firm*—Koppel & Jacobs

(57) ABSTRACT

The dodecamethyl closo-borane dianion [closo-B$_{12}$(CH$_3$)$_{12}$]$^{2-}$ and anion [closo-B$_{12}$(CH$_3$)$_{12}$]$^-$ were synthesized and characterized. Dodecamethyl-closo dodecaborate (2–) was produced from [closo-B$_{12}$H$_{12}$]$^{2-}$, using trimethylaluminum, and methyl iodide and modified Friedel-Crafts reaction conditions. The anion was produced from the dianion by chemical oxidation using ceric (4) ammonium nitrate in acetonitrile. The anion and dianion were both characterized by $^1$H and $^{11}$B NMR spectroscopy, high-resolution fast atom bombardment (FAB) mass spectrometry, cyclic voltammetry, and single-crystal X-ray diffraction. The "camouflaged" polyhedral borane anion [closo-B$_{12}$(CH$_3$)$_{12}$]$^{2-}$, can be used as a precursor to materials that offer a broad spectrum of novel applications ranging from drug applications and supramolecular chemistry to use as a weakly-coordinating dianion.

7 Claims, 1 Drawing Sheet

SYNTHESIS OF PERMETHYLDODECABORATE AND PARAMAGNETIC DODECABORATE SALT

The present invention relates to unique three-dimensional methylated icosahedral boron cage compounds This invention was made with support under Contract Number DE-FG02-9ER61975 awarded by the U.S. Department of Energy. The Government has certain rights in the invention.

BACKGROUND

Hawthorne et al has reported the preparation of closo-1, 12-$C_2B_{10}(CH_3)_{12}$ and other octamethyl $C_2$ boranes.(Jiang, W., Knobler, C. B., Mortimer, M. D., Hawthorne, M. F., Angew. Chem., 1995, 34, 1332.). The permethylated icosahedral carboranes [closo-$CB_{11}(CH_3)_{12}$]$^{31}$, and the uncharged blue radical closo-$CB_{11}(CH_3)_{12}$ derived from that anion, has been reported by Michl et al. (King, B. T., Zanousek, B. G., Trammell, M., Noll. B. C., Michl, J., J Am. Chem. Soc., 1996, 118, 3313) Additionally, other persubstituted polyboron compounds are known.

The most prominent persubstituted polyboron compounds is the polyhydroxylated boron compound, boric acid, $B(OH)_3$. Alkaline solutions of $B(OH)_3$ deposit $Na_2[B_4O_5(OH)_4]\cdot nH_2O$, which constitute two abundant boron minerals, kernite (n=2) and borax (n=8) (F. A. Cotton, G. Wilkinson, Advanced Inorganic Chemistry, 5th ed., Wiley, New York, 1988, pp. 164–169). Other common boron structures include the trigonal and tetrahedral boron-oxygen units common to borate minerals (G. A. Heller, Top. Curr. Chem. 1986, 131, 39–98) and the icosahedron. The allotropes of elemental boron, (J. Donohue, The Structures of the Elements, Wiley, New York, 1974, pp. 48–82), boron-rich solids (H. Hubert, B. Devouard, L. A. J. Garvie, M. O'Keeffe, P. R. Buseck, W. T. Petuskey, P. F. McMillan, Nature 1998, 391, 376–378) and the parent anion of the polyhedral boranes, [closo-$B_{12}H_{12}$]$^{2-}$ (J. A. Wunderlich, W. N. Lipscomb, J Am. Chem. Soc. 1960, 82, 4427–4428) all contain $B_{12}$ icosohedra.

The charge-delocalized icosohedral ion [closo-$B_{12}H_{12}$]$^{2-}$ may be considered as the parent aromatic species for borane chemistry in a manner similar to that served by the benzene ring in organic (carbon) chemistry. Isoelectronic substitution of one or two :B-H vertices in [closo-$B_{12}H_{12}$]$^{2-}$ by :C-H$^+$ provides the aromatic derivatives [closo-1-$CB_{11}H_{12}$]$^-$, and a set of three isomeric dicarbacarboranes (1,2– or ortho; 1,7– or meta; and 1,12– or para) closo-$C_2B_{10}H_{12}$ R (N. Grimes, Carboranes, Academic Press, New York, 1970, p. 8). Each of these isoelectronic derivatives of [closo-$B_{12}H_{12}$]$^{2-}$, undergoes characteristic hydrogen-substitution reactions at their B-H vertices resulting in a huge number of known icosahedral species (Hawthorne, M. F., "Carborane Chemistry at Work and Play", Proceedings of the Ninth International Meeting on Boron Chemistry published in Advances in Boron Chemistry, Seibert, W. (Ed.), The Royal Society of Chemistry, London, 1996, 261–272)

Of special interest are derivatives in which every available B-H vertex has been substituted. Thus, hydrophobic derivatives of [closo-$B_{12}H_{12}$]$^{2-}$ and [closo-1-$CB_{11}H_{12}$]$^-$, and the three isomeric diboranes, such as [closo-$B_{12}Cl_{12}$]$^{2-}$ (Knoth, W. H., Miller, H. C., Sauer, J. C., Balthis, J. H., Chia, Y. T., Muetterties, E. L., Inorg, Chem, 1964, 3, 159–167), [closo-$CB_{11}(CH_3)_{12}$]$^-$, (King, B. T.; Janousek, Z.; Grüner, B.; Trammell, M.; Noll, B. C.; Michl, J. J. Am. Chem. Soc. 1996, 118, 10902–10903) and closo-1,12-$C_2B_{10}$($CH_3$)$_{12}$, (W. Jiang, C. B. Knobler, M. D. Mortimer, M. F. Hawthorne, Angew. Chem. 1995, 107, 1470–1473; Angew. Chem. Int. Ed. Engl. 1995, 34, 1332–1334.) have been synthesized. The existence and formulation of similar highly substituted polyhedral borane derivatives having hydrophilic substituents, such as hydroxyl have most recently been demonstrated by Hawthorne and Peyman ("Aromatic Polyhedra Hydroxyborates: Bridging Boron Oxides and Boron Nitrides", Angew. Chem. Int. Ed., 1999,38, 1061–1064).

U.S. Pat. No. 3,551,120 to Miller, et.al. discloses the formation of numerous ionic icosahedral substituted boranes of the general formula $M_a(B_{12}H_{12-y}X_y)_b$, with y=1–12, and U.S. Pat. No. 3,390,966 to Knofl et. al. discloses the formation of numerous ionic carboranes of the general formula $M_a(B_{10}H_{10-y}X_y)_b$, with y=1–10, where b=1 to 3. However, examples of the analogous closo-borane dianions [closo-$B_n(CH_3)_n$]$^{2-}$ (n=6–12) have not been reported.

Paramagnetic persubstituted polyhedral closo-boranes such as [closo-$B_6X_6$]$^-$ (Heinrich, A, Keller, H. L., Preetz, W. Z. Naturforsch., Teil B., 1990, 45, 184) and [closo-$B_9X_9$]$^-$ (Wong, E. H., Kabbani, R. M., Inorg. Chem., 1990, 45, 184) where X is Cl, Br or I and [closo-$CN_{11}Me_{12}$]$^-$ (B. T. King, B. T., Noll, B. C., McKinley, A. J., Michl, J., J. Am. Chem. Soc., 1996. 118. 10902) have also been reported. These species were obtained via metal-ion oxidation of the corresponding reduced borane clusters. In each case, solutions of these paramagnetic species are moderately stable, but decolorize after prolonged contact with air.

Many researchers have sought globular structures possessing both hydrophobic surfaces and extraordinary kinetic stability with which to synthesize supramolecular structures, weakly-coordinating anions and space-controlling drug components. The fullerenes, characterized by unique chemistry and physical properties, represent one family of such precursors. Another family of globular hydrophobes, referred to as "camouflaged" carboranes, have been described in the literature (Jiang, W.; Knobler, C. B.; Hawthorne, M. F. Angew. Chem., Int. Ed. Engl. 1995, 34, 1332–1334; King, B. T.; Janousek, Z.; Grüner, B.; Trammell, M.; Noll, B. C.; Michl, J. J. Am. Chem. Soc. 1996, 118, 3313–3314; Herzog, A.; Maderna, A.; Knobler, C. B.; Hawthorne, M. F. Chem. Eur. J. 1999, 5,1212–1217). These species may approach the van der Waals diameter of $C_{60}$ by attachment of methyl groups and functionalized methyl substituents to the icosahedral scaffolding of the aromatic [closo-$C_nB_{12-n}H_{12}$]$^{n-2}$ (n=1 or 2). Whereas hydrophobic and amphiphilic derivatives of this sort are known with n=1 or 2, the fully methylated derivative of the parent species, dodecamethyl-closo-dodecaborate(2–), (n=0), has not been shown.

BEIEF DESCRIPTION OF DRAWINGS

DETAILED DESCRIPTION

Figure 1:
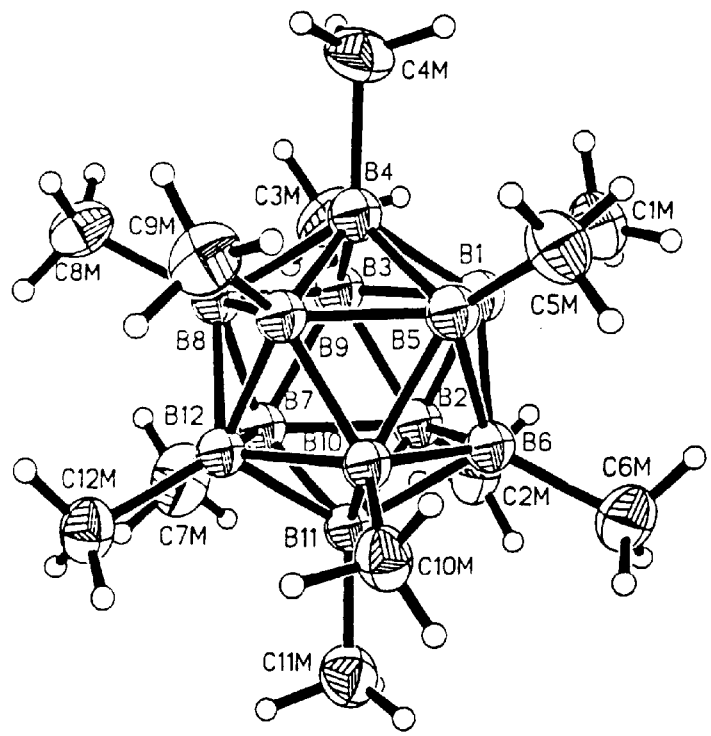
FIG. 1 shows the molecular structure of the dodecamethyl-closo-dodecaborate(2–) anion [closo-$B_{12}(CH_3)_{12}$]$^{2-}$.

The closo-borane dianions [closo-$B_n(CH_3)_n$]$^{2-}$ (n=6–12) have now been made using a new permethylation technique. Icosahedral closo-boranes are treated with trimethylaluminum and methyl iodide in the absence of a solvent. This method produced the permethyldodecaborate ion, [closo-$B_{12}(CH_3)_{12}$]$^{2-}$, dodecamethyl-closo-dodecaborate(2–) and the paramagnetic compound, [closo-$B_{12}(CH_3)_{12}$]$^-$ when applied to the parent anion of the polyhedral borane family, aromatic [closo-$B_{12}H_{12}$]$^{2-}$. The anion and dianion were characterized by $^1$H and $^{11}$B NMR spectroscopy, high-resolution fast atom bombardment (FAB) mass spectrometry, cyclic voltammetry, and single-crystal X-ray diffraction.

The prior art describes the reaction of methyl trifluoromethanesulfonate or aluminum chloride/methyl iodide with carboranes (Jiang, W.; Knobler, C. B.; Hawthorne, M. F. *Angew. Chem., Int. Ed. Engl.*, 1995, 34, 1332–1334; King, B. T.; Janousek, Z.; Grüner, B.; Trammell, M.; Noll, B. C.; Michl, *J. Am. Chem. Soc.* 1996, 118, 3313–3314.; Herzog, A.; Maderna, A.; Knobler, C. B.; Hawthorne, M. F. *Chem. Eur. J*, 1999, 5,1212–1217). However, when methyl trifluoromethanesulfonate was added to [N(n-Bu)$_4$]$_2$[closo-$B_{12}H_{12}$]$^{2-}$ only partial triflation was obtained and only partial halogenation resulted when aluminum chloride/methyl iodide was used. It has now been found that a mixture of [closo-$B_{12}H_{12}$]$^{2-}$, trimethylaluminum, and methyl iodide held at 45° C. for about 20 to 150 hours produced various polyiodinated species [closo-$B_{12}Me_{12-x}I_x$]$^{2-}$ (5≤x≤12). Heating of the suspension at 45° C. for about 6 days(140–150 hours) gave a mixture of [closo-$B_{12}(CH_3)_{12}$]$^{2-}$, and [closo-$B_{12}(CH_3)_{11}I$]$^{2-}$. This mixture was then isolated and again heated at the reflux temperature in neat trimethylaluminum to convert the by-product [closo-$B_{12}(CH_3)_{12-x}I_x$]$^{2-}$ into [closo-$B_{12}(CH_3)_{12}$]$^{2-}$. The blue colored, air stable paramagnetic ion closo-$B_{12}(CH_3)_{12}^-$ is then easily obtained from the dianion by chemical oxidation using ceric(4)-ammonium nitrate in acetonitrile (CAN).

Following CAN oxidation of [NBu$^n_4$]$_2$[closo-$B_{12}(CH_3)_{12}$] (TBA)$_2$[closo-$B_{12}(CH_3)_{12}$] in acetonitrile, the anion [closo-$B_{12}(CH_3)_{12}$]$^-$ was isolated as a PPN salt in 66% yield. Reduction of [closo-$B_{12}(CH_3)_{12}$]$^-$ with NaBH$_4$ in ethanol regenerated $B_{12}(CH_3)_{12}^{2-}$ in good yield.

To prepare (Ph$_3$P=N=PPh$_3$)[closo-$B_{12}(CH_3)_{12}$] a sample of [NBu$^n_4$]$_2$, also known as (TBA)$_2$, (0.23 g, 0.29 mmol) was dissolved in acetonitrile (5 ml) and an acetonitrile solution (5 ml) of ceric(IV) ammonium nitrate (0.16 g, 0.29 mmol) was added. The reaction mixture, which immediately turned deep blue, was stirred for 5 min and then added to 50 ml of water. The precipitate was separated by filtration, dissolved in ethanol (10 ml) and again filtered. (Ph$_3$P=N=PPh$_3$)Cl (1.70 g., 2.90 mmol) dissolved in ethanol (10 ml) was added to the filtrate. Upon cooling overnight at about 0° C. dark blue (Ph$_3$P=N=PPh$_3$)[closo-$B_{12}(CH_3)_{12}$] (0.16 g., 0.19 mmol., 66% yield) separated by crystallization.

It appears that the iodine atoms of the B-I vertices are successively exchanged by methyl groups when the species [closo-$B_{12}Me_{12-x}I_x$]$^{2-}$ (x≤5) are heated in trimethylaluminum. This was verify by heating the monoiodinated anion [closo-$B_{12}H_{11}I$]$^{2-}$ to reflux in neat trimethylaluminum and [closo-$B_{12}H_{11}(CH_3)$]$^{2-}$ was obtained in 55% yield. This procedure provides an alternate route to monoalkylated [closo-$B_{12}H_{11}R$]$^{2-}$ anions, which are usually obtained through palladium-catalyzed alkylation of [closo-$B_{12}H_{11}I$]$^{2-}$ with Grignard reagents (Peymann, T.; Knobler, C. B.; Hawthorne, M. F. *Inorg. Chem.* 1998, 37, 1544–1548). No reaction was observed when [PPh$_4$]$_2$[closo-$B_{12}I_{12}$] was heated for 4 days in neat trimethylaluminum at the reflux temperature.

The NMR data for [closo-$B_{12}(CH_3)_{12}$]$^{2-}$ ($^{11}$B NMR: singlet at −10.8 ppm, $^1$H NMR: broad singlet at −0.48 ppm) is in accordance with its symmetry (point group I$_h$). Because of quadrapole moment of the boron nucleus, a $^{13}$C NMR resonance for the B-CH$_3$carbon atoms of [closo-$B_{12}(CH_3)_{12}$]$^{2-}$ was not obtained. High-resolution FAB mass spectrometry confirmed the mass of the permethylated derivative [closo-$B_{12}(CH_3)_{12}$] (centered at m/z= 310.4020 with the correct isotopic distribution). The cyclic voltammogram of [Et$_4$N]$_2$[closo-$B_{12}(CH_3)_{12}$] (100 mM Et$_4$NPF$_6$, Ag/AgCl, acetonitrile) shows a reversible one-electron oxidation process [closo-$B_{12}(CH_3)_{12}$]$^{2-}$/[closo-$B_{12}$]$^-$ at E$_{1/2}$=0.41 V. The dinegative species [closo-$B_{12}$(CH$_3$)$_{12}$]$^{2-}$ is more easily oxidized than the monoanion [closo-$CB_{11}(CH_3)_{12}$]$^-$ (E$_{pa}$=1.6 V) (King, B. T.; Janousek, Z.; Grüner, B.; Trammell, M.; Noll, B. C.; Michl, J. *J. Am. Chem. Soc.* 1996, 118, 3313–3314).

The dodecamethyl closo-borane anion [closo-$B_{12}(CH_3)_{12}$]$^-$ can be produced by
a) heating a solution of [closo-$B_{12}H_{12}$]$^{2-}$, trimethylaluminum, and methyl iodide at 45° C. for about 140 to about 150 hours to produce a mixture of [closo-$B_{12}(CH_3)_{12}$]$^{2-}$ and [closo-$B_{12}(CH_3)_{11}I$]$^{2-}$
b) heating the mixture at reflux temperature in neat trimethylaluminum to produce [closo-$B_{12}(CH_3)_{12}$]$^{2-}$, and
c) reacting [closo-$B_{12}(CH_3)_{12}$]$^{2-}$ with ceric(4) ammonium nitrate in acetonitrile to produce [closo-$B_{12}(CH_3)_{12}$]$^-$.

By starting with [closo-$B_nH_n$]$^-$, where n=6–12, various different compounds of the formula [closo-$B_n(CH_3)_n$]$^-$ can be produced.

The anion [closo-$B_{12}(CH_3)_{12}$]$^-$ was characterized by high resolution fast atom bombardment mass spectrometry (HR-FAB-MS), electron paramagnetic resonance (EPR). UV-VIS spectroscopy and cyclic voltammetry. Furthermore, the crystal structure of [Ph$_3$P=N=PPh$_3$closo-$B_{12}(CH_3)_{12}$] was determined by single crystal X-ray diffraction. Negative HR-FAB-MS: found: mlz=310.4022: calc. 310.4014. Crystal data for (Ph$_3$P=N=PPh$_3$)[closo-$B_{12}(CH_3)_{12}$] is: $C_{48}H_{66}B_{12}NP_2$, M=878.04, monoclinic. a=3466(3), b=934.2 (8), c=1869(2) pm. U=5.120(7)nm$^3$, T=298°K, space group C2/cZ=4 $\mu$(Mo-K$\alpha$)=1.2 cm$^{-1}$. 4900 unique reflections were measured, 2489 reflections were considered observed [I>2α (I)] and all data was used in all calculations. The final R factor (R=Σ| |F$_o$|−|F$_c$||/Σ|F$_o$.) was 0.066 (for 2489 independent reflections). The structure was solved using statistical methods and refined by full-matrix least squares on F$^2$.CCDC 182/1405. Crystallographic files are available in cif format at http://www.rsc.org/suppdata/cc/1999/2039/

Blood-red single-crystals of [(C$_5$H$_5$N)$_2$CH$_2$]closo-$B_{12}$(CH$_3$)$_{12}$] CH$_3$CN. (orthorhombic Pc2$_1$n, a=971.5(7) pm, b=1505.2(10) pm, c=2281.9(15) pm; Z=4; R=0.074, R$_w$= 0.184; GOF=1.04) were obtained from acetonitrile/ethanol. The crystal structure of [closo-$B_{12}(CH_3)_{12}$]$^{2-}$, shown in FIG. 1, confirms the permethylation of the B12 icosahedron with some distortion of its icosahedral geometry. The thermal ellipsoids in FIG. 1 represent a 30% probability level. The selected bond distances (pm) of the anion are: B-B= 174.0(14)–181.1(14); B-C=159.1(14)–170.4(13). The B-B bond lengths of [closo-$B_{12}(CH_3)_{12}$]$^{2-}$ are similar to the bond distances of the unsubstituted anion [closo-$B_{12}H_{12}$]$^{2-}$, reported by Wunderlich and Lipscomb (175.5(7)–178.0(7) pm (Wunderlich, J. A.; Lipscomb, W. N. *J. Am. Chem. Soc.* 1960, 82, 4427–4428). The B-C bond distances of [closo-$B_{12}(CH_3)_{12}$]$^{2-}$ are longer than the B-C bond of [closo-$B_{12}H_{11}(CH_3)$]$^{2-}$, (158(2) pm; Peymann, T.; Knobler, C. B.; Hawthorne, M. F. *Inorg. Chem.* 1998, 37, 1544–1548), the exo B-C bonds of [closo-$CB_{11}(CH_3)_{12}$]$^-$ (159(2)160.1(6) pm (King, B. T.; Janousek, Z.; Grüner, B.; Trammell, M.;

Noll, B. C.; Michl, J., *J. Am. Chem. Soc.* 1996, 118, 3313–3314) and closo-1,12-$C_2B_{10}(CH_3)_{12}$ (158.3(6) pm (Jiang, W.; Knobler, C. B.; Hawthorne, M. F. *Angew. Chem., Int. Ed Engl.* 1995, 34, 1332–1334). The red color of $[(C_5H_5N)_2CH_2][closo-B_{12}(CH_3)_{12}]$ is apparently due to a charge-transfer interaction of the anion $[closo-B_{12}(CH_3)_{12}]^{2-}$ with the pyridinium rings of the dipositive cation. The plane through the triangle B1, B4, and B5 is nearly parallel to the plane established by a pyridinium ring N1 and C2 through C6. The angle between the normals of these two planes is 7.3°. The distances of the boron atoms B1, B4, and B5 from the latter plane are 508(1), 486(1), and 504(1) pm, respectively and the distances of the methyl carbon atoms C1M, C4M, and C5M are 389(1), 338(1), and 378(1) pm, respectively.

The longest across-cage methyl carbon-methyl carbon distances of $[closo-B_{12}(CH_3)_{12}]^{2-}$ average 668 pm; the corresponding maximum methyl hydrogen-methyl hydrogen distance is 761 pm compared to 707 pm for $C_{60}$ (Liu, S.; Lu, Y.; Kappes, M. M.; Ibers, J. A. *Science* 1991, 254, 408–410).

The radicals differ significantly in reactivity as their persistence largely depends upon the unpaired electron's chemical and physical environment. (Griller, D., Ingold, K. U., *Acc.,Chem.Res*, 1976, 9.13). A major effect that stabilizes paramagnetic species is steric crowding. A radical center surrounded by bulky groups is more persistent than similar species without this protection. This deep blue radical-anion is surprisingly stable with respect to reaction with oxygen.

A solid sample of $(Ph_3P=N=PPh_3)[closo-B_{12}(CH_3)_{12}]$ exhibits an EPR signal with g=2.0076. The UV-VIS spectrum (FIG. 1) of the blue salt $[NEt_4][closo-B_{12}(CH_3)_{12}]$ (TEA2) in acetonitrile displays absorption in the visible region.

Cyclic voltammetry (100 mM $NEt_4PfF_6$, Ag/AgCl, MeCN) of $[closo-B_{12}(CH_3)_{12}]^{31}$ reveals a reversible wave with E½=0.44 V for the one-electron process 2+e⁻→1. The reduction potential of $[closo-B_{12}(CH_3)_{12}]^-$ matches the corresponding oxidation potential previously determined for $[closo-B_{12}(CH_3)_{12}]^{2-}$. The X-ray crystal structure (FIG. 2) confirms that $[closo-B_{12}(CH_3)_{12}]^-$ is a permethylated monoanionic closo-borane.

Figure 2:
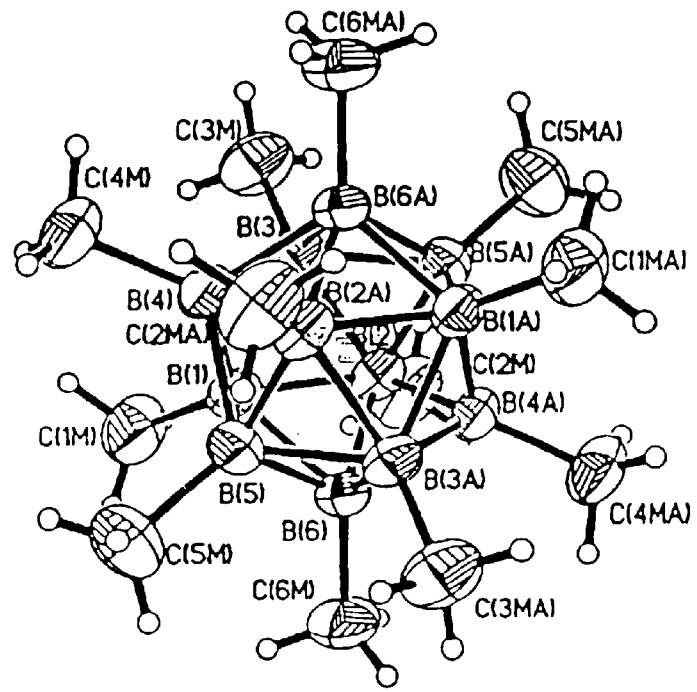
FIG. 2 shows the molecular structure of the dodecamethyl-closo-dodecaborate(1–) anion [closo-$B_{12}(CH_3)_{12}$]$^-$.

The crystal structure of the anion is shown in FIG. 2. in the solid state, the anionic cluster of $(Ph_3P=N=PPh_3)$ $[closo-B_{12}(CH_3)_{12}]^-$ is less distorted from icosahedral symmetry than the dianionic species $[closo-B_{12}(CH_3)_{12}]^-$ studied as a $[(Ph_3P=N=PPh_3)C_5H_4N)_2 CH^2]^{2+}$ salt [B-B bond lengths: $[closo-B_{12}(CH_3)_{12}]^-$=178.5(8)–180.5(7)pm; $[closo-B_{12}(CH_3)_{12}]^{2-}$=174(1-B-C bond lengths: $[closo-B_{12}(CH_3)_{12}]^-$=159.8(9)–161.3(8)pm; 1$[closo-B_{12}(CH_3)_{12}]^{2-}$=159(1)-170(1) pm]. The maximum across-cage methyl carbon separations average 668 pm for the dianionic species compared to 663 pm for the monoanion. The greater distortion of $[closo-B_{12}(CH_3)_{12}]^{2-}$ may be explained by the charge-transfer interaction of the dipositive $[[closo-B_{12}(CH_3)_{12}](C_5H_4N)_2CH_2]^{2+}$ counter ion and the dianion. This interaction is suggested by the unique color of the blood-red $[closo-B_{12}(CH_3)_{12}(C_5H_4N)CH_2]$ salt.

Because the new dodecaborate moieties, $[closo-B_{12}(CH_3)_{12}]^{2-}$ and the paramagnetic ion $[closo-B_{12}(CH_3)_{12}]^-$, are weakly coordinated anions with lipophilic properties they are suitable for extraction of radioactive metal ions from nuclear waste. For example, the $[closo-B_{12}(CH_3)_{12}]^{2-}$ ion forms hydrocarbon soluble salts with cations such as cesium and strontium. $[closo-B_{12}(CH_3)_{12}]^{2-}$ dissolved in kerosene or other hydrocarbon solvents can be used to extract $^{137}Cs^+$ and $^{90}Sr^{2+}$ from aqueous radioactive waste. A representative extraction formula, where M is the extracted metal, is as follows:

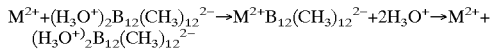

The crude waste acid water phase is mixed with permethyldodecaborate salt. The hydrocarbon phase will then contain the complexed metal. Water was then mixed with the hydrocarbon phase to strip out the $M^{2+}$ and regenerate the $H_3O^+$ salt dissolved in water.

Also the permethyldodecaborates can serve as precursors for new pharmacophores, resulting in new drugs. Still further, they can be used to produce stabilized unilamellar boron-containing liposomes for delivery to tumors for boron neutron capture therapy. The paramagnetic lipophilic anion, because of its blue color and response to a magnetic or electric field, is further useful in sensor systems to detect easily oxidized or reduced compounds and, because it can function as an reversible electron trap (oxidant) could be incorporated in electrochemical systems.

$[closo-B_{12}(CH_3)_{12}]^-$ presents unique possibilities inherent in the concept of camouflaged polyhedral boranes. Here the persubstitution stabilizes an unusual oxidation state that has not been obtained from the 'naked' parent species $[closo-B_{12}H_{12}]^{2-}$. Upon electrochemical oxidation ($E_{1/2}$1.43 V vs SCE), the dianion instead dimerizes by an undetermined mechanism with loss of one exo H-atom and dimerization of $B_{12}$-cages to form the B-H-B bridge of $[B_{24}H_{23}]^{3-}$ (Wiersema, R. J., Middaugh, R. L., *Inorg. Chem.*, 1969, 8. 2074):

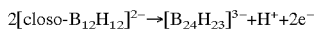

The latter species is structurally related to $[a^2-B_{20}H_{19}]^{3-}$. (Watson-Clark, R. A., Knobler, C. B. and Hawthorne, M. F., *Inorg. Chem.*, 1996, 35, 2963). This reaction pathway is not available for the permethylated radical.

A further advantage of the disclosed anions and there preparation are that they are easy to synthesize and therefore much less costly then prior available compounds such as produced by Michl. The anions disclosed herein are readily derived from $(B_{12}H_{12})^{2-}$. The Michl species is expensive to make because it is derived from closo-$(CB_{11}H_{12})^-$ which is difficult, and therefore expensive, to produce. Additionally, the water solubility of the resultant compounds provides a novel starting molecule for drug design. Other $B_nH_n^{2-}$ ions, for example $B_{10}H_{10}^{2-}$, might be permethylated using the above described procedure. Metallocarborane and metalloborane anions are expected to undergo the same reactions and are possible substrates for methylation using this procedure, It is further contemplated that compounds such as N-bromo- or N-chlorosuccinimide could be used in the described procedure to produce a halomethyl derivative, such as $[B_{12}(CH_3)_{11}CH_2Cl]^{2-}$.

We claim:
1. Dodecamethyl closo-borane dianion $[closo-B_{12}(CH_3)_{12}]^{2-}$.
2. Dodecamethyl closo-borane anion, $[closo-B_{12}(CH_3)_{12}]^-$.
3. A method of producing the dodecamethyl closo-borane dianion $[closo-B_{12}(CH_3)_{12}]^{2-}$ comprising
   a) heating a solution of $[closo-B_{12}H_{12}]^{2-}$, trimethylaluminum, and methyl iodide at 45° C. for about 140 to about 150 hours to produce a mixture of $[closo-B_{12}(CH_3)_{12}]^{2-}$ and $[closo-B_{12}(CH_3)_{11}]^{2-}$, and
   b) heating the mixture at reflux temperature in neat trimethylaluminum to produce $[closo-B_{12}(CH_3)_{12}]^{2-}$.

4. A method of producing the dodecamethyl closo-borane anion [closo-$B_{12}(CH_3)_{12}$]$^-$ comprising:
   a) heating a solution of [closo-$B_{12}H_{12}$]$^{2-}$, triethylaluminun, and methyl iodide at 45° C. for about 140 to about 150 hours to produce a mixture of [closo-$B_{12}(CH_3)_{12}$]$^{2-}$ and [(closo-$B_{12}(CH_3)_{11}I$]$^{2-}$,
   b) heating the mixture at reflux temperature in neat trimethylaluminum to produce [closo-$B_{12}(CH_3)_{12}$]$^{2-}$, and
   c) reacting [closo-$B_{12}(CH_3)_{12}$]$^{2-}$ with ceric(4) ammonium nitrate in acetonitrile to produce [(closo-$B_{12}(CH_3)_{12}$]$^-$.

5. The method of producing the methylated closo-borane dianions [closo-$B_{12}Me_{12-x}I_x$]$^{2-}$ where x is from 5 to 12 comprising, heating a solution of [closo-$B_{12}H_{12}$]$^{2-}$, trimethylaluminum, and methyl iodide at 45° C. for a period of time greater than about 20 but less than about 150 hours.

6. A method of producing a methyl closo-borane dianion [closo-$B_n(CH_3)_n$]$^{2-}$ where n=6–12, comprising:
   a) heating a solution of [closo-$B_nH_n$]$^{2-}$, trimethylaluminum, and methyl iodide at 45° C. for about 140 to about 150 hours to produce a mixture of [closo-$B_n(CH_3)_n$]$^{2-}$ and [closo-$B_n(CH_3)_{n-1}I$]$^{2-}$, and
   b) heating the mixture at reflux temperature in neat trimethylaluminum to produce [closo-$B_n(CH_3)_n$]$^{2-}$.

7. A method of producing a methyl closo-borane anion [closo-$B_n(CH_n)_{12}$]$^-$ where n=6–12, comprising:
   a) heating a solution of [closo-$B_nH_n$]$^{2-}$, trimethylaluminum, and methyl iodide at 45° C. for about 140 to about 150 hours to produce a mixture of [closo-$B_n(CH_3)_n$]$^{2-}$ and [closo-$B_n(CH_3)_{n-1}I$]$^{2-}$,
   b) heating the mixture at reflux temperature in neat trimethylaluminum to produce [closo-$B_n(CH_3)_n$]$^{2-}$, and
   c) reacting [closo-$B_n(CH_3)_n$]$^{2-}$ with ceric(4) ammonium nitrate in acetonitrile to produce [closo-$B_n(CH_3)_n$]$^-$.

* * * * *